US008055515B2

(12) United States Patent
Kusakabe

(10) Patent No.: US 8,055,515 B2
(45) Date of Patent: Nov. 8, 2011

(54) INFORMATION PROCESSING APPARATUS, INFORMATION PROCESSING METHOD, AND COMPUTER PROGRAM

(75) Inventor: Yuki Kusakabe, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 1011 days.

(21) Appl. No.: 11/565,068

(22) Filed: Nov. 30, 2006

(65) Prior Publication Data
US 2007/0136376 A1    Jun. 14, 2007

(30) Foreign Application Priority Data

Dec. 6, 2005    (JP) .................................. 2005-352208

(51) Int. Cl.
G06Q 10/00    (2006.01)
(52) U.S. Cl. ................................. 705/3; 705/2
(58) Field of Classification Search .................... 705/2, 3
See application file for complete search history.

(56) References Cited

U.S. PATENT DOCUMENTS

| 2002/0042742 | A1* | 4/2002 | Glover et al. ........... 705/14 |
| 2003/0236683 | A1* | 12/2003 | Henderson et al. ........... 705/2 |
| 2005/0159977 | A1* | 7/2005 | Green et al. ........... 705/2 |
| 2006/0149416 | A1* | 7/2006 | Mohapatra et al. ........... 700/242 |
| 2007/0088594 | A1* | 4/2007 | Goodall et al. ........... 705/9 |
| 2007/0088664 | A1 | 4/2007 | Nakano |

FOREIGN PATENT DOCUMENTS

| JP | 2002-222258 A | 8/2002 |
| JP | 2003-263501 A | 9/2003 |
| JP | 2004-029896 A | 1/2004 |
| JP | H06-312010 A | 1/2004 |
| WO | 2005/057465 A2 | 6/2005 |

* cited by examiner

Primary Examiner — Robert Morgan
Assistant Examiner — Maroun Kanaan
(74) Attorney, Agent, or Firm — Canon U.S.A., Inc. I.P. Division

(57) ABSTRACT

An information processing apparatus and a method for managing dispensing information associated with a prescription for medicine, the apparatus and method including inputting acquiring information for acquiring dispensing status information associated with a prescription for medicine, sending the input acquiring information to at least one other device, and receiving the dispensing status information acquired based on the acquiring information from the at least one other device.

17 Claims, 21 Drawing Sheets

FIG.9

| NAME OF PHARMACY | WAITING TIME | BUSINESS HOURS | MAP | DETAIL INFORMATION |
|---|---|---|---|---|
| PHARMACY "A" | 0 min | 8:00~20:00 | http:// | DETAIL ABOUT "A" |
| PHARMACY "B" | 5 min | 9:00~19:00 | http:// | DETAIL ABOUT "B" |
| PHARMACY "C" | 3 min | 9:00~19:00 | http:// | DETAIL ABOUT "C" |

FORWARD    CANCEL

DISPLAY

FIG.10

| NAME OF PHARMACY | WAITING TIME | BUSINESS HOURS | MAP | DETAIL INFORMATION |
|---|---|---|---|---|
| PHARMACY "A" | 10 min | 8:00~20:00 | http:// | DETAIL ABOUT "A" |
| PHARMACY "B" | 5 min | 9:00~19:00 | http:// | DETAIL ABOUT "B" |
| PHARMACY "C" | 20 min | 9:00~19:00 | http:// | DETAIL ABOUT "C" |

FORWARD    CANCEL

DISPLAY

FIG.11

| PHARMACY "A" | | |
|---|---|---|
| WAITING NUMBER | STATUS | EXPECTED TIME |
| No. 1 | "BEFORE DISPENSING" | 10 min |
| No. 2 | "ALREADY DISPENSED". NOT HERE YET | 1 min |
| No. 3 | "BEFORE DISPENSING". HERE | 5 min |
| No. 4 | "BEFORE DISPENSING" | 15 min |
| No. 5 | "BEFORE DISPENSING" | 15 min |
| | TOTAL MINUTES | 46 min |

OK   CANCEL

DISPLAY

FIG.12

EXPECTED TIME TO COME TO PHARMACY

⦿ TOMORROW OR AFTER TOMORROW  [1 ⇕] DAY(S) AFTER

○ TODAY   ABOUT [15 ⇕] : [00 ⇕]

ANY OTHER

☑ MORE REQUEST FOR PRESCRIPTION MEDICATIONS TOGETHER ( SEND )   ( CANCEL )

DISPLAY

FIG.13

YOUR SUBMISSION HAS BEEN SUCCESSFULLY SENT.

YOU CAN MAKE SURE THE STATUS OF YOUR

PRESCRIPTION FROM THE FOLLOWING URL.

http://xxx.co.jp/05021/xx.html

PRESCRIPTION ID:6382965

CLOSE

DISPLAY

| PATIENT NAME | PRESCRIPTION ID | URL | DISPENSING STATUS | INSURANCE NUMBER | EXPECTED TIME TO COME TO PHARMACY |
|---|---|---|---|---|---|
| TARO YAMADA | 6382965 | http:// | BEFORE DISPENSING | 123456789 | 2005/8/10 12:30 |
| | | | | | |

| PATIENT NUMBER | NAME | ADDRESS | E-MAIL ADDRESS | INSURANCE NUMBER | NAME OF DISEASE | GROUP ID |
|---|---|---|---|---|---|---|
| 123456 | TARO YAMADA | KANAGAWA PREFECTURE | xxx@co.jp | 123456789 | COLD | Ab456789 |

FIG.21

| NAME OF MEDICINE | EFFECT | DOSAGE REGIMEN |
|---|---|---|
| abc | REDUCE FEVER | ONE TABLET AFTER EACH MEAL |
| def | RELIEVE MUSCLE ACHES | TWO TABLETS BEFORE SLEEPING |
| ghi | REDUCE FEVER | ONE TABLET BEFORE EACH MEAL |

INFORMATION PROCESSING APPARATUS, INFORMATION PROCESSING METHOD, AND COMPUTER PROGRAM

BACKGROUND OF THE INVENTION

1. Field of the Invention

The present invention relates to an information processing apparatus, an information processing method, and a program for sending/receiving data to/from an external device.

2. Description of the Related Art

A prescription describes a medicine prescribed for a patient as a result of a diagnosis in a medical institution, such as a hospital and a clinic.

Generally speaking, a patient gets a prescription issued by a medical institution, and takes the prescription to an external pharmacy that is open outside the medical institution. Then, the pharmacy dispenses a medicine in accordance with the prescription, and the patient receives the dispensed medicine. In this case, the pharmacy does not know the medication contents to be dispensed until it gets the prescription. Only after the patient takes the prescription to the pharmacy can the pharmacy begin dispensing a medicine.

To shorten the time for a patient to wait in a pharmacy, a prescription may be sent to the pharmacy in advance by fax, and a medicine may be dispensed before the patient goes to the pharmacy. According to this method, the patient does not know how busy the pharmacy is at the time of sending the prescription thereto. Therefore, even if the medical institution or doctor sends the prescription beforehand, the patient might still have to wait in the pharmacy. Another problem is that it is difficult to select an optimum external pharmacy from a plurality of external pharmacies.

Japanese Patent Application Laid-Open No. 2003-263501 discusses a method for shortening the time for a patient to wait in a pharmacy when a prescription is sent beforehand. According to this method, a display unit of a prescription sending apparatus displays a map of each external pharmacy and the time to wait for the dispensation in the pharmacy. Then, a patient specifies one pharmacy and the time to pick up a medicine when the patient sends a prescription to the specified pharmacy using the prescription sending apparatus.

However, the dispensation of the prescription is not necessarily done in sequential order. The medication may not be dispensed sequential order due to the contents of the received prescription. For example, the medicine for a patient of a serious case is dispensed on a priority basis. Thus, dispensing of the medication may not necessarily be completed on time as estimated.

According to Japanese Patent Application Laid-Open No. 2003-263501, after the prescription is sent to the pharmacy, the patient does not know the general dispensing (preparation) status of the sent prescription in the pharmacy, and does not know the dispensing status of the sent prescription in real time. Additionally, it is very difficult for a patient to change the selected pharmacy once the prescription has been sent to the pharmacy. In addition, in many instances due to the patient's schedule, it is also difficult to change when the patient is able to go to the pharmacy to pick up the prescription.

SUMMARY OF THE INVENTION

The present invention is directed to a prescription transmission system in which a patient can dynamically know the dispensing status in a pharmacy, and can change the pharmacy to a desired one and/or the desired time to pick up the dispensed medicine, after having sent a prescription to the pharmacy.

According to an aspect of the present invention, an information processing apparatus configured to receive dispensing status information associated with a prescription for medicine from at least one other device configured to update the dispensing status information in accordance with a dispensing status includes an input unit configured to input acquiring information for acquiring the dispensing status information, a sending unit configured to send the acquiring information to the at least one other device, and a receiving unit configured to receive, from the at least one other device, the dispensing status information acquired based on the acquiring information.

According to another aspect of the present invention, an information processing apparatus includes a first receiving unit configured to receive prescription data, a first sending unit configured to send information based on the prescription data to at least one other device, a second receiving unit configured to receive the information from at least one other device, and a second sending unit configured to send dispensing status information to the at least one other device in accordance with the information received by the second receiving unit.

According to yet another aspect of the present invention, an information processing apparatus includes an updating unit configured to update dispensing status information associated with a prescription for medicine, wherein the dispensing status information includes a dispensing time and a sending unit configured to send the dispensing status information to at least one other device if the dispensing time is greater than predetermined time.

According to yet another aspect of the present invention, an information processing apparatus includes an input unit configured to input patient information, an authentication unit configured to authenticate the patient information using previously stored patient information, and a display unit configured to display, when the patient information is authenticated, an expected time when a prescription associated with the patient information will be filled.

According to yet another aspect of the present invention, an information processing apparatus includes a first input unit configured to input patient information, a second input unit configured to input an expected time to pick-up a prescription, an authentication unit configured to authenticate the patient information against previously stored patient information, a display unit configured to display, when the patient information is authenticated, an expected time when a prescription associated with the patient information will be filled.

According to an exemplary embodiment of the present invention, a patient can dynamically know a dispensing status in a pharmacy after having sent a prescription to the pharmacy. Even if the dispensation is not done in a sequential order due to the contents of the prescriptions, the patient can know the accurate dispensing time. Even after the prescription has been sent to the pharmacy, the patient can change the time to pick up the medicine or cancel the pharmacy. Thus, the patient can go to receive the medicine at the convenience of the patient.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute apart of the specification, illustrate exemplary embodiments, features, and aspects of the invention and, together with the description, serve to explain the principles of the invention.

FIG. 9 illustrates an example of a screen displayed on a display unit in the first exemplary embodiment.

FIG. 10 illustrates an example of a screen displayed on the display unit in the first exemplary embodiment.

FIG. 11 illustrates an example of a screen displayed on the display unit in the first exemplary embodiment.

FIG. 12 illustrates an example of a screen displayed on the display unit in the first exemplary embodiment.

FIG. 13 illustrates an example of a screen displayed on the display unit in the first exemplary embodiment.

FIG. 14 illustrates a prescription table in the first exemplary embodiment.

FIG. 15 illustrates a patient information table in the first exemplary embodiment.

FIG. 21 illustrates a medicine effect table in the sixth exemplary embodiment.

DETAILED DESCRIPTION OF THE EMBODIMENTS

Various exemplary embodiments, features, and aspects of the invention will be described in detail below with reference to the drawings. In the exemplary embodiments, an image forming apparatus is adopted as an information processing apparatus that sends and receives prescriptions.

First Exemplary Embodiment

Figure 1:
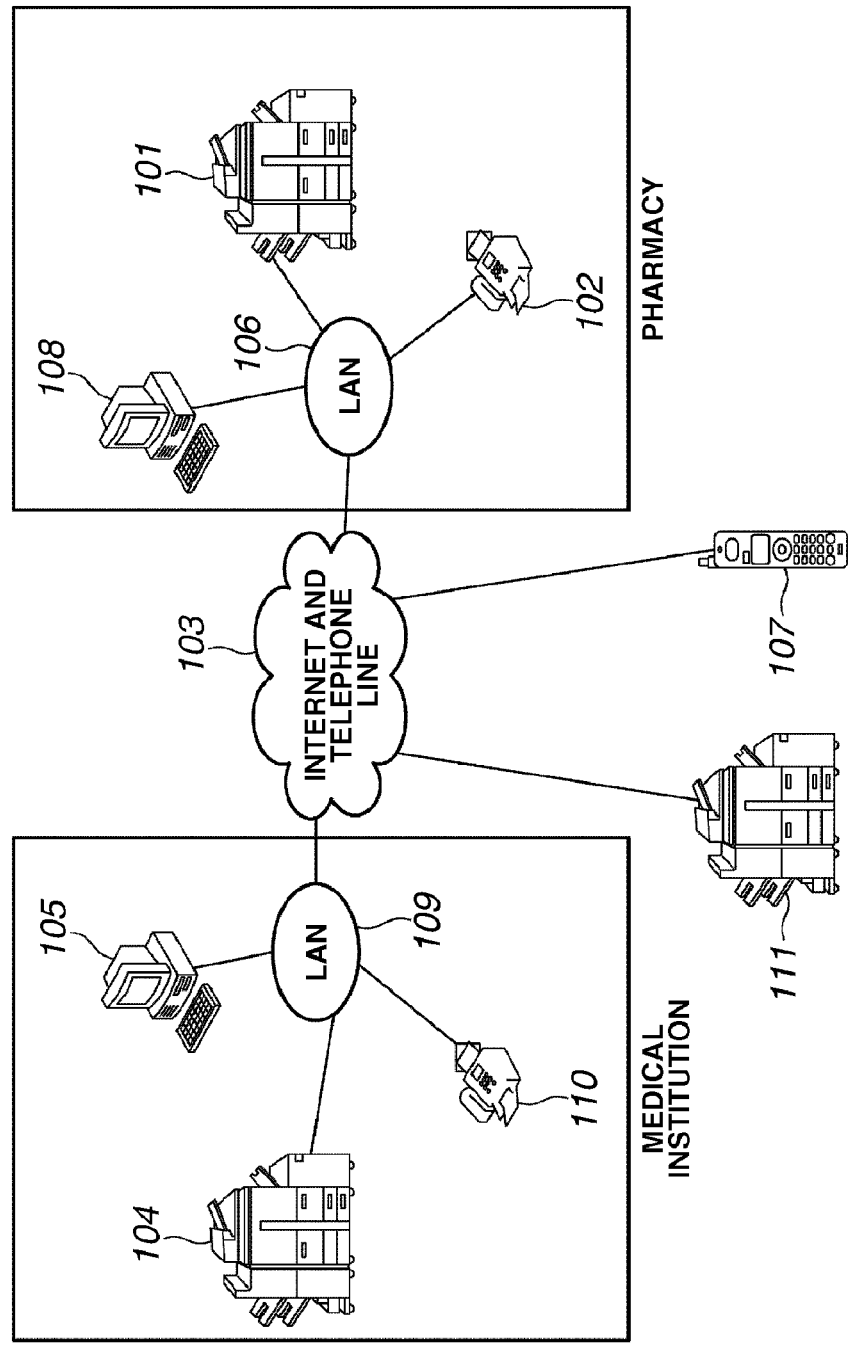
FIG. 1 is a configuration diagram of a prescription transmission system in a first exemplary embodiment of the present invention.

FIG. 1 is a configuration diagram of a prescription transmission system that sends prescriptions to an image forming apparatus in (or at) a pharmacy from an image forming apparatus in (or at) a medical institution in a first exemplary embodiment of the present invention.

As illustrated in FIG. 1, in the present exemplary embodiment, an image forming apparatus 104 in a medical institution, an image forming apparatus 101 in a pharmacy, a portable terminal 107, such as a cell phone, and a remotely located image forming apparatus 111 all connected with each other through the Internet and a telephone line 103. In the medical institution, the image forming apparatus 104, a FAX device 110, and a data processing apparatus 105, such as a personal computer (PC), are connected with each other through a local area network (LAN) 109. In the pharmacy, the image forming apparatus 101, a FAX device 102, and a data processing apparatus 108, such as a PC, are connected with each other through a LAN 106. The data processing apparatuses 105 and 108 may be medical computers (so-called a medical statement computer). These devices connected to the LANs 106 and 109 can communication with each other using a predetermined protocol.

Figure 2:
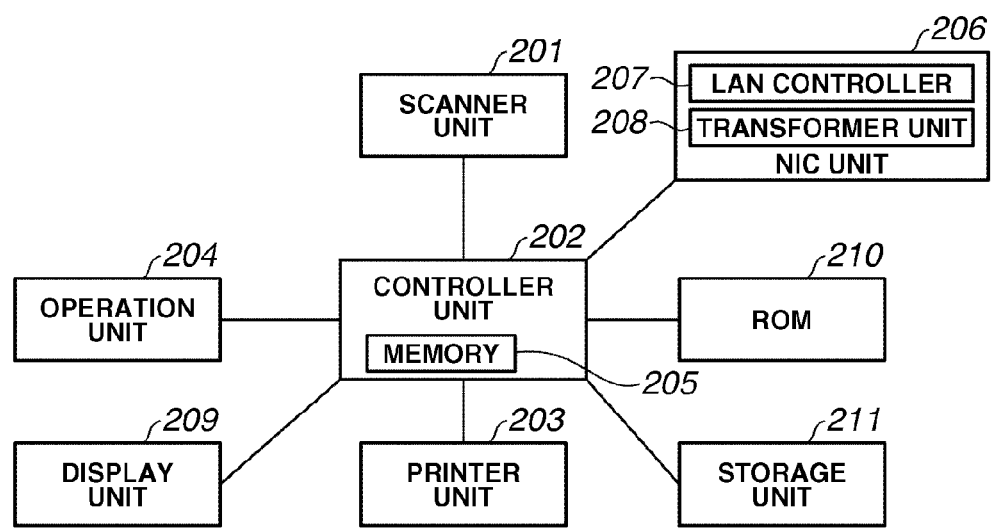
FIG. 2 is a schematic block diagram of an image forming apparatus in the first exemplary embodiment.

FIG. 2 is a schematic block diagram of the image forming apparatuses 101 and 104 according to the present embodiment. In the present embodiment, the image forming apparatuses 101 and 104 are digital multifunction peripherals having general functions of COPY, PRINT, FAX, etc.

As illustrated in FIG. 2, each of the image forming apparatuses 101 and 104 includes a scanner unit 201 and a controller unit 202. The scanner unit 201 performs a document reading process. The controller unit 202 performs image processing for image data read by the scanner unit 201, and stores the image data in a memory 205. Further, each of the image forming apparatuses 101 and 104 includes an operation unit 204, a ROM 210 and a storage unit 211, such as a hard disk drive or a memory card. The operation unit 204 sets various printing conditions for the image data read by the scanner unit 201. Each of the image forming apparatuses 101 and 104 further includes a printer unit 203 configured to form an image using the image data read out of the memory 205 on a recording sheet in accordance with a print setting condition set by the operation unit 204.

Further, each of the image forming apparatuses 101 and 104 also includes a network interface card (NIC) unit 206. In the NIC unit 206, a LAN controller 207 controls all the processing for monitoring communication packets flowing through a particular LAN (e.g., LANs 106, 109), acquiring information on the LAN, and sending the data read by the scanner unit 201 to one LANs 106, 109, and the network 103. A transformer unit 208 transforms a voltage to realize physical communications between the image forming apparatus and the LAN.

The controller unit 202 is connected to a display unit 209, and controls the display unit 209 to display print setting conditions. The display unit 209 of the image forming apparatus 104 installed in the medical institution displays, among other things, maps of external pharmacies or detail information about the pharmacies. The display unit 209 may be a touch panel, but any type of display that would enable practice of the present invention is applicable. The storage unit 211 of the image forming apparatus 101 in the pharmacy stores a waiting time information table. The waiting time information table stores information regarding the time period since a prescription is received until the dispensed medicine is given to a patient, and is constantly updated in accordance with the number of received prescriptions. The number of received prescriptions is determined with reference to a prescription table 1401 as described below. The waiting time information table may also be stored in a storage unit 215 or RAM 212 of the data processing apparatus 108.

Figure 3:
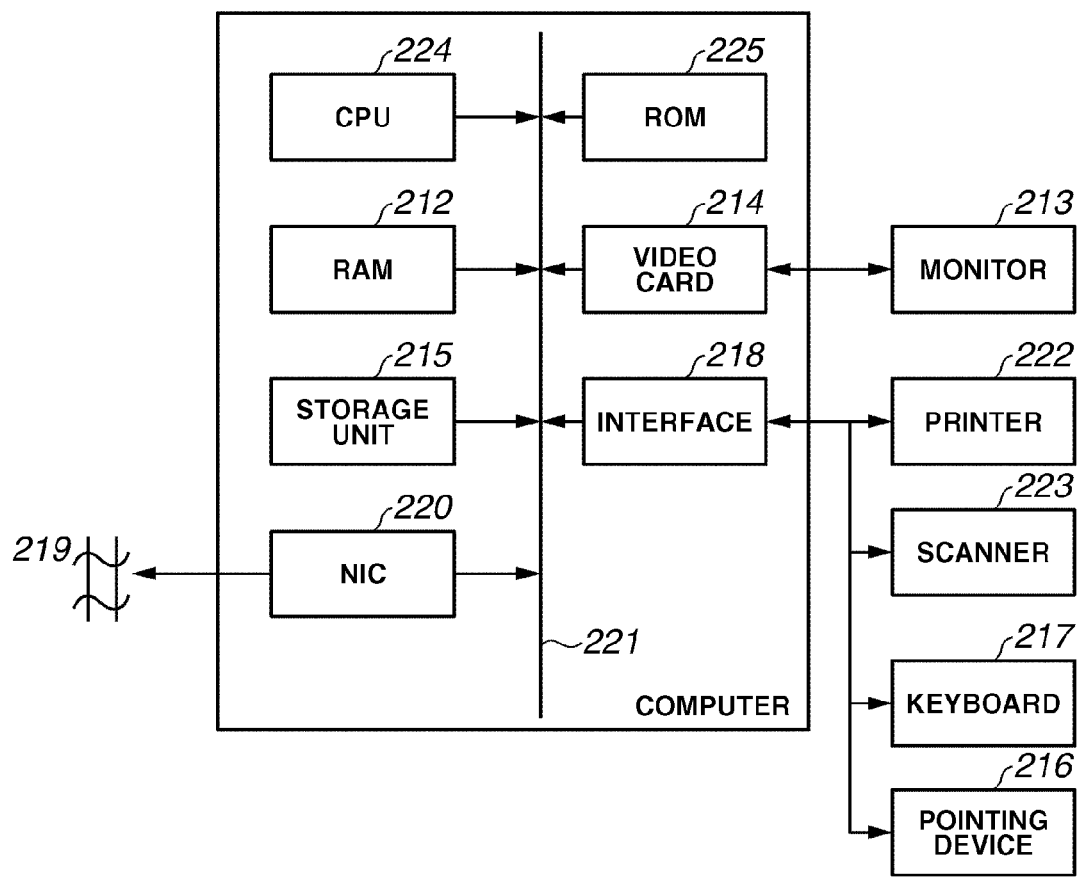
FIG. 3 is a schematic block diagram of a data processing apparatus in the first exemplary embodiment.

FIG. 3 is a schematic block diagram of the data processing apparatuses 105 and 108 in the present embodiment. Each of the data processing apparatuses 105 and 108 includes a CPU 224, a ROM 225, a RAM 212, a video card 214 for connecting with a monitor 213 (e.g., touch panel, CRT, etc.), and a storage unit 215, such as a hard disk drive or memory card. Each of the data processing apparatuses 105 and 108 further includes an interface 218 (e.g., a USB, IEEE1394) for connecting to external devices such as a keyboard 217, a pointing device 216 (e.g., mouse, stylus, etc.), a printer 222, and a scanner 223. Further, each of the data processing apparatuses 105 and 108 includes a network interface card (NIC) 220 for connecting with a network 219. The elements of each of the data processing apparatuses 105 and 108 are connected to each other through a system bus 221.

The CPU 224 loads a program stored in the ROM 225 or storage unit 215 into the RAM 212 (work memory) to execute the program. The CPU 224 controls each of the above-described elements through the system bus 221 in accordance with the program.

FIG. 15 illustrates an example of a patient information table 1501 stored in the storage unit 211 of the image forming apparatus 104 in the medical institution. The patient information table 1501 contains patient information stored on a patient-by-patient basis. The patient information table 1501 includes, but is not limited to, a patient name, an address, an e-mail address, an insurance number, a name of a disease, and a group ID in association with each patient number. The patient number is a patient ID given to each patient. The group ID refers to a particular group, such as a family. With this group ID, the medicines for a plurality of patients having the same group ID can be received at the same time in the pharmacy. In addition to being stored in the storage unit 211 of the imaging forming apparatus 104 in the medical institution, the patient information table 1501 can also be stored in the data processing apparatus 105 in the medical institution.

FIG. 14 illustrates an example of a prescription table 1401 stored in the storage unit 211 of the image forming apparatus 101 in the pharmacy. In association with each prescription, the prescription table 1401 stores a patient name, a prescription ID corresponding to a prescription, a URL for confirming the dispensing status of the prescription, a dispensing status, an insurance number, and an expected (estimated) time for the user to come to the pharmacy. The prescription ID corresponding to a prescription is set by the controller unit 202 of the image forming apparatus 101 when the image forming apparatus 101 receives the prescription from the medical institution.

The dispensing status indicates "before dispensing" if the prescription is received from the medical institution and has not yet been given to the pharmacist to fill. The dispensing status represents "being dispensed", if the prescription has been given to the pharmacist. The dispensing status indicates "already dispensed", if the pharmacist has filled the prescription. The dispensing status is updated when the pharmacist or a pharmacy staff member accesses and rewrites the prescription table 1401 using either the image forming apparatus 101 or the data processing apparatus 108.

The dispensing status of the prescription table 1401 can be updated to "being dispensed" by scanning the prescription and reading the prescription ID added to the prescription when the pharmacy staff gives the prescription to the pharmacist. Further, if the pharmacist scans the prescription after having filled the prescription, the dispensing status can be updated to "already dispensed". In addition to storing the prescription table 1401 in the storage unit 211 of the image forming apparatus 101, the prescription table 1401 can also be stored in the data processing apparatus 108. In this case, the prescription ID is set by the CPU 224 at the time the prescription is stored in the data processing apparatus 108.

Figure 4:
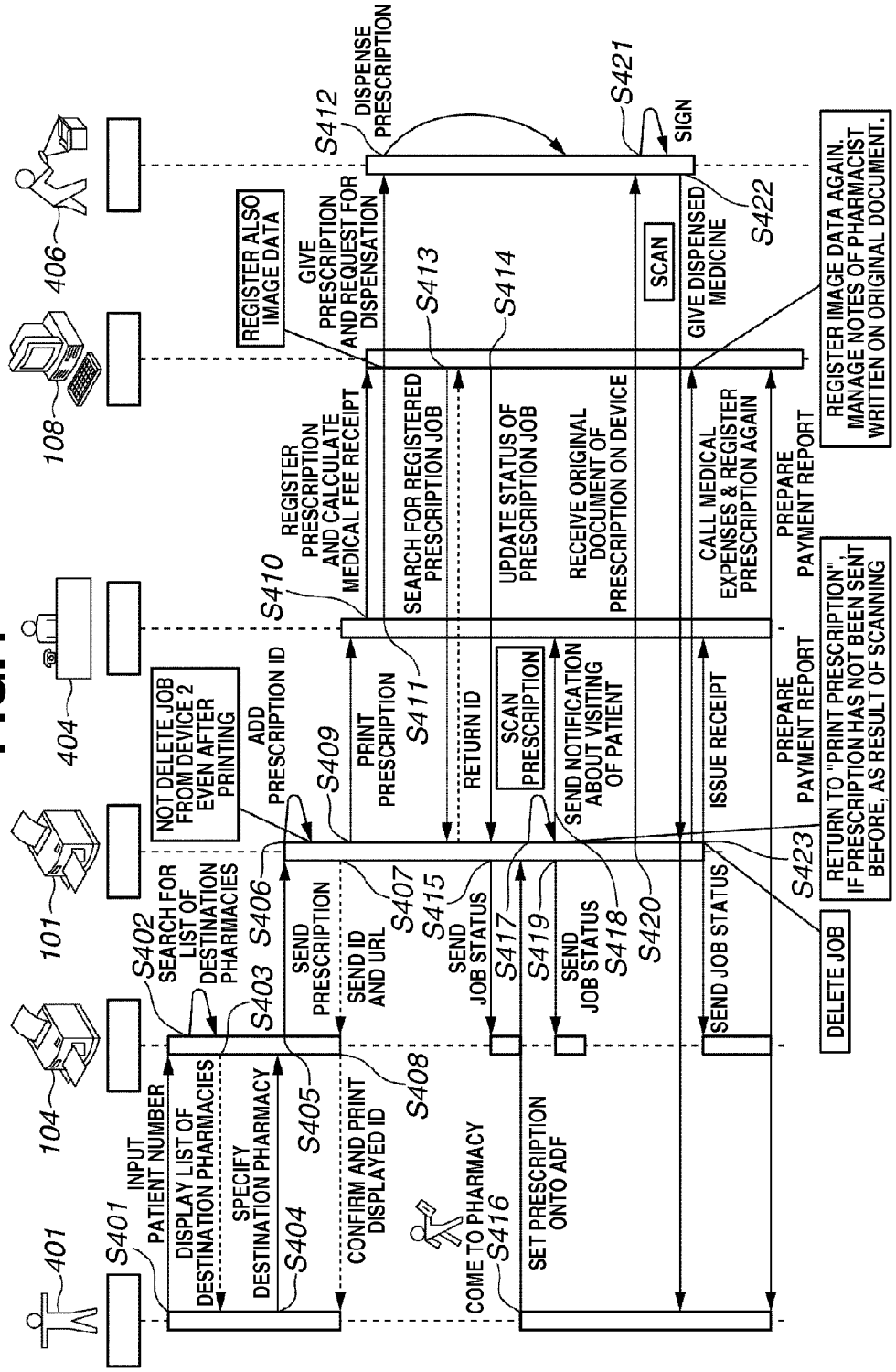
FIG. 4 is a diagram illustrating the process flow of the prescription transmission system in the first exemplary embodiment.

The prescription transmission system of the present embodiment will now be described with reference to FIG. 4. In FIG. 4, reference numeral 401 denotes a patient, reference numeral 104 is the image forming apparatus installed a medical institution, reference 101 is the image forming apparatus installed in a pharmacy, reference numeral 404 denotes a pharmacy staff member, reference numeral 108 is the data processing apparatus in the pharmacy used to calculate the fee associated with a particular prescription, and reference numeral 404 denotes a pharmacist who fills the prescription
(Process for Sending a Prescription from a Medical Institution to a Pharmacy)

Steps S401 through S404 describe the process flow in which a patient 401 sends a prescription from the image forming apparatus 104 installed in the medical institution to the image forming apparatus 101 installed in the pharmacy.

First, in step S401, the patient 401 inputs a patient number via the operation unit 204 of the image forming apparatus 104. When the patient information is authenticated based on the patient information table 1501 stored in the storage unit 211 of the image forming apparatus 104, a search for external pharmacies occurs in step S402. At this time, the image forming apparatus 104 sends a waiting time inquiry signal to the image forming apparatus 101 of all external pharmacies located within a predetermined distance from the medical institution, and receives a present waiting time from the waiting time information table stored in the image forming apparatus 101 of each pharmacy.

In step S403, the display unit 209 of the image forming apparatus 104 displays a list of external pharmacies as illustrated in FIG. 10. In step S404, the patient 401 specifies, via the operation unit 204, a pharmacy to send the prescription to. In step S405, the prescription is read by the scanner unit 201 of the image forming apparatus 104 and is sent to the image forming apparatus 101 of the pharmacy specified in step S404.
(Process for Receiving a Prescription Sent from the Medical Institution in the pharmacy, adding a prescription ID thereto, and Registering the Prescription)

Steps 406 and S407 describe a process for receiving the prescription sent from the medical institution through the image forming apparatus 101 in the pharmacy, adding a prescription ID thereto, and registering the prescription having the prescription ID added thereto and the prescription ID in the prescription table 1401.

In step S406, the image forming apparatus 101 in the pharmacy receives the prescription sent from the medical institution. At this time, the image forming apparatus 101 adds a specific prescription ID to the prescription, and registers the prescription having the prescription ID added thereto together with the prescription ID in the prescription table 1401. At this time, the dispensing status of the prescription is also registered. Specifically, the status of "before dispensing" is registered. In addition, a URL for confirming the dispensing status of the prescription is created, and the created URL is also registered in the prescription table 1401. Then, in step S407, the image forming apparatus 101 sends the prescription ID and the URL corresponding to the received prescription along with a transmission completion notification to the image forming apparatus 104.
(Process for Confirming the Prescription ID and the URL Corresponding to a Prescription by the Medical Institution)

Step S408 describes a process for confirming the prescription ID and the URL corresponding to the prescription sent from the medical institution to the pharmacy and the dispensing status of the prescription using the image forming apparatus 104 of the medical institution.

More specifically, in step S408, the image forming apparatus 104 receives the transmission completion notification, the prescription ID, and the URL corresponding to the prescription. Then, the patient 401 confirms the prescription ID and the URL shown in the transmission completion notification. Next, the patient prints the received ID and the URL. The patient can then access the URL using a portable terminal 107 or a remotely located image forming apparatus 111, thus confirming the dispensing status of the prescription, changing the pharmacy to a different one from which the patient receives the medicine, or changing the time to pick up the medicine.

(Process Conducted in the Pharmacy Based on the Received Prescription)

Steps S409 through S415 describe a process for receiving a prescription in the pharmacy using the data processing apparatus 108 based on the contents of the prescription.

Upon completion of step S407, in step S409, the pharmacy staff member 404 prints the prescription. In step S410, the pharmacy staff member 404 registers the printed prescription and the prescription ID in the data processing apparatus 108, and conducts a process for calculating a medical fee receipt using the data processing apparatus 108. In this case, the prescription data may be transferred and registered into the data processing apparatus 108, when the prescription is received through the image forming apparatus 101.

In step S411, the pharmacy staff member 404 provides the prescription to the pharmacist 406 in charge of dispensing the prescription. Also in step S411, the pharmacy staff member 404 registers information representing that a request to fill the received prescription in the prescription table 1401.

Next, in step S412, the pharmacist 406 dispenses the prescription. In step S413, the data processing apparatus 108 searches for prescription data from the prescription table 1401 of the image forming apparatus 101, using a corresponding prescription ID. In step S414, the status of the prescription data is updated to "being dispensed". In step S415, the image forming apparatus 101 sends information representing that the status of the prescription data has been updated, to the image forming apparatus 104. Note that, in step S411, the prescription can be scanned using the image forming apparatus 101, thus identifying the prescription ID or the insurance number so as to update the dispensing status of the prescription data.

(Process to be Conducted when a Patient Comes to a Pharmacy with a Prescription)

Steps S416 through S423 describe a process conducted in the pharmacy when the patient 401 comes to the pharmacy with a prescription.

In steps S416 and S417, the patient 401 comes to the pharmacy and scans the prescription using the image forming apparatus 101. In step S418, a patient name and/or insurance number of the scanned prescription is identified, and the prescription table 1401 is used to confirm whether the scanned prescription was sent in advance or is being read for the first time. If the prescription was sent in advance, the image forming apparatus 101 notifies the data processing apparatus that the patient corresponding to the previously sent prescription is at the pharmacy.

The monitor of the data processing apparatus 108 displays information indicating that the patient is at the pharmacy, thus notifying the pharmacy staff member 404 or the pharmacist 406 that the patient corresponding to a previously sent prescription is at the pharmacy. The pharmacy staff member 404 or the pharmacist 406 then confirms the status of the prescription. If the prescription has been filled, the pharmacy staff member 404 or the pharmacist 406 provides the patient 401 with the medicine.

In step S417, if the patient scans the prescription, then in step S419, a notification indicating that the patient is at the pharmacy is sent to the image forming apparatus 104. In step S420, the pharmacist 406 receives the original document of the prescription from the patient, signs the prescription in step S421, and gives the medicine to the patient in step S422. The pharmacy staff member 404 or the pharmacist 406 then updates the status of the prescription to "already dispensed" via the image processing apparatus 108. The data processing apparatus 108 then provides the image forming apparatus 104 with the updated status. Further, the corresponding prescription data is deleted from the prescription table 1401. When the medicine is given to the patient, the status can be updated by scanning the prescription using the image forming apparatus 101. At the time the medicine is given to the patient, a receipt is issued in step S423, and a payment report is prepared by the pharmacy staff member 404.

Figure 5:
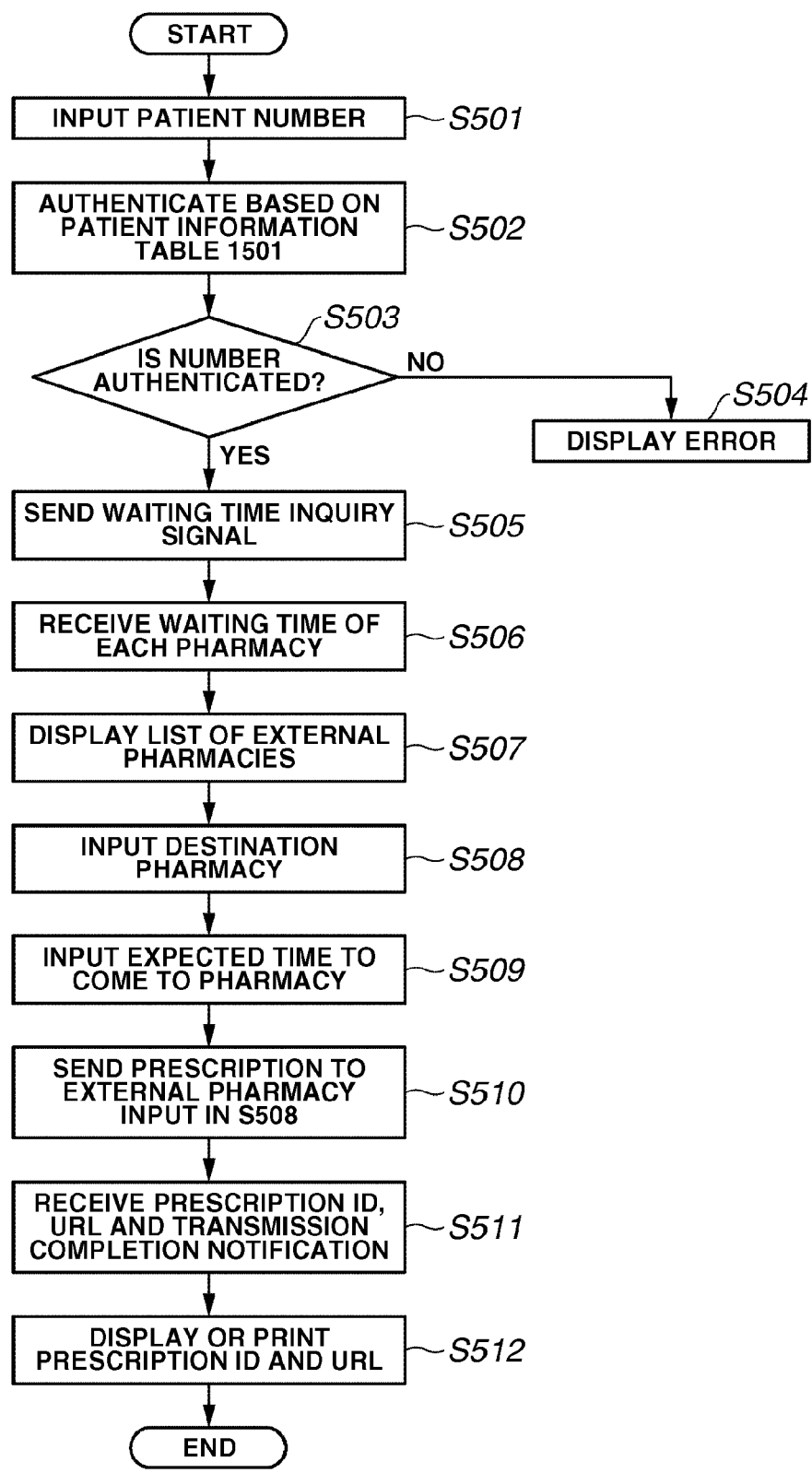
FIG. 5 is a flowchart of a process executed by an image forming apparatus in a medical institution in the first exemplary embodiment.

FIG. 5 is a flow diagram of a process, performed by the image forming apparatus 104, for selecting a pharmacy where the prescription is to be sent.

In step S501, a patient number is input via the operation unit 204 of the image forming apparatus 104. In step S502, an authentication process is performed based on the patient number of the patient information table 1501 stored in the image forming apparatus 104. In step S503, if the patient number is authenticated, the flow proceeds to step S505. On the other hand, if the patient number is not authenticated, the flow proceeds to step S504, where an authentication error is displayed on display unit 209. In step S505, the image forming apparatus 104 sends a waiting time inquiry signal to the image forming apparatuses 101 of all pharmacies located within a predetermined distance from the medical institution.

In step S506, the image forming apparatus 104 receives the current waiting time from each of the pharmacies to which the waiting time inquiry signal was sent. In step S507, the display unit 209 displays a list of all the pharmacies that provided a current waiting time, the waiting times, the business hours, map/direction information, and detail information as illustrated in FIG. 10. If the detail information of each pharmacy displayed in step S507 is specified, the display unit 209 displays the waiting number, the dispensing status, and the expected waiting time associated with each respective prescription currently being handled by the specified pharmacy as illustrated in FIG. 11.

Figure 16:
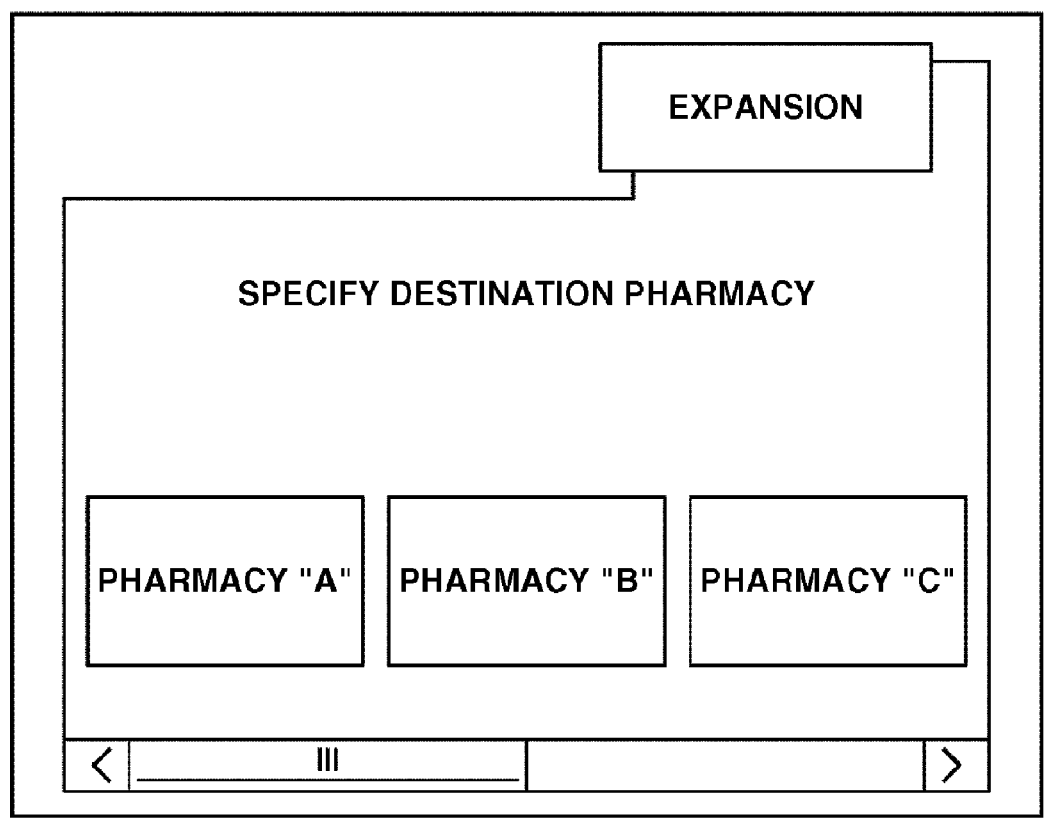
FIG. 16 illustrates an example of a screen displayed on the display unit in the first exemplary embodiment.

In step S508, the patient 401, using a user interface illustrated in FIG. 16, selects a pharmacy that the prescription should be sent to, and the selected pharmacy is input to the image forming apparatus 104. In step S509, the patient 401, using the user interface illustrated in FIG. 12, inputs the expected time the patient 401 plans to be at the pharmacy. The patient 401 can input any expected time as long as the time is after the expected waiting time and within the pharmacy's business hours. If any other prescriptions have already been requested, medicines of a patient having the same group ID can be dispensed and received together. In step S510, the prescription is sent to the pharmacy selected in step S508.

If a prescription ID corresponding to the received prescription is issued, the image forming apparatus 101 sends the prescription ID, a URL for confirming the dispensing status of the prescription, and a transmission completion notification to the image forming apparatus 104. In step S511, the prescription ID, the URL, and the transmission completion notification are received by the image forming apparatus 104. In step S512, the prescription ID and the URL are displayed on the display unit 209 as illustrated in FIG. 13. In addition, the prescription ID and the URL can also be printed. The patient 401 can either write down the ID and URL information or can take the printed ID and URL. Note that the ID and the URL can be sent to the patient's e-mail address, cell phone, or any other contact location registered as patient information in advance in the patient information table 1501.

The patient 401 can access the URL using the portable terminal 107 or the image forming apparatus 111 to confirm the dispensing status of the medicine corresponding to the sent prescription. By accessing the URL, the patient 401 may change the pharmacy, the expected time the patient 401 plans to be at the pharmacy, or may cancel the visit to the pharmacy.

Figure 6:
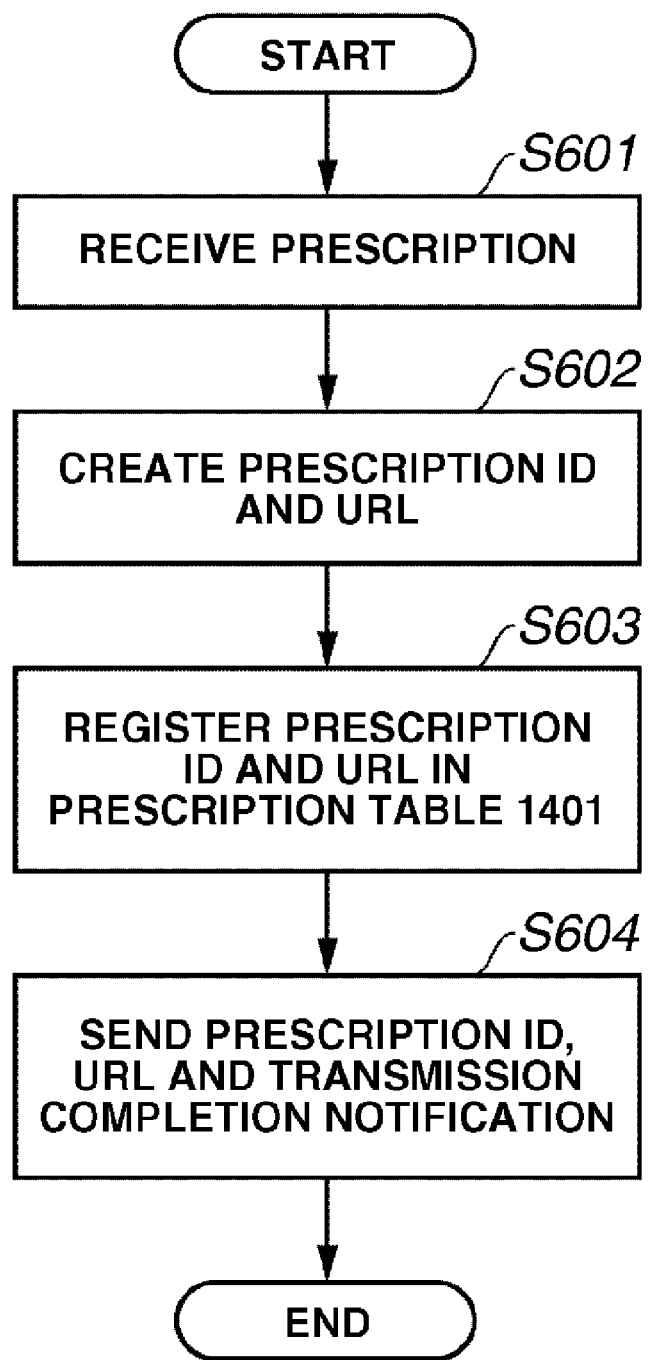
FIG. 6 is a flowchart of a process executed by an image forming apparatus in a pharmacy in the first exemplary embodiment.

FIG. 6 is a flow diagram of a prescription process performed by the image forming apparatus 101. First, in step S601, the image forming apparatus 101 receives the prescription sent from the image forming apparatus 104. Next, in step S602, the image forming apparatus 101 issues a specific prescription ID for the received prescription and creates a URL for confirming the prescription ID and the status of the prescription. In step S603, the image forming apparatus 101 registers the patient name, the prescription ID, the URL, the dispensing status, the insurance number, etc., in the prescription table 1401 stored in the storage unit 211. In step S604, the image forming apparatus 101 sends the prescription ID, the URL, and the transmission completion notification to the image forming apparatus 104 that issued the prescription.

In the present embodiment, a dispensing status of "before dispensing" is registered in the prescription table 1401. Once the process of filling the prescription begins, the status is updated to "being dispensed". When the medication has been dispensed, the status is updated to "already dispensed". In the present embodiment, the pharmacy staff member 404 or the pharmacist 406 updates the dispensing status in the prescription table 1401 via the operation unit 204 of the image forming apparatus 101 or the data processing apparatus 108. The dispensing status may also be updated by scanning the prescription using the image forming apparatus 101.

Figure 7:
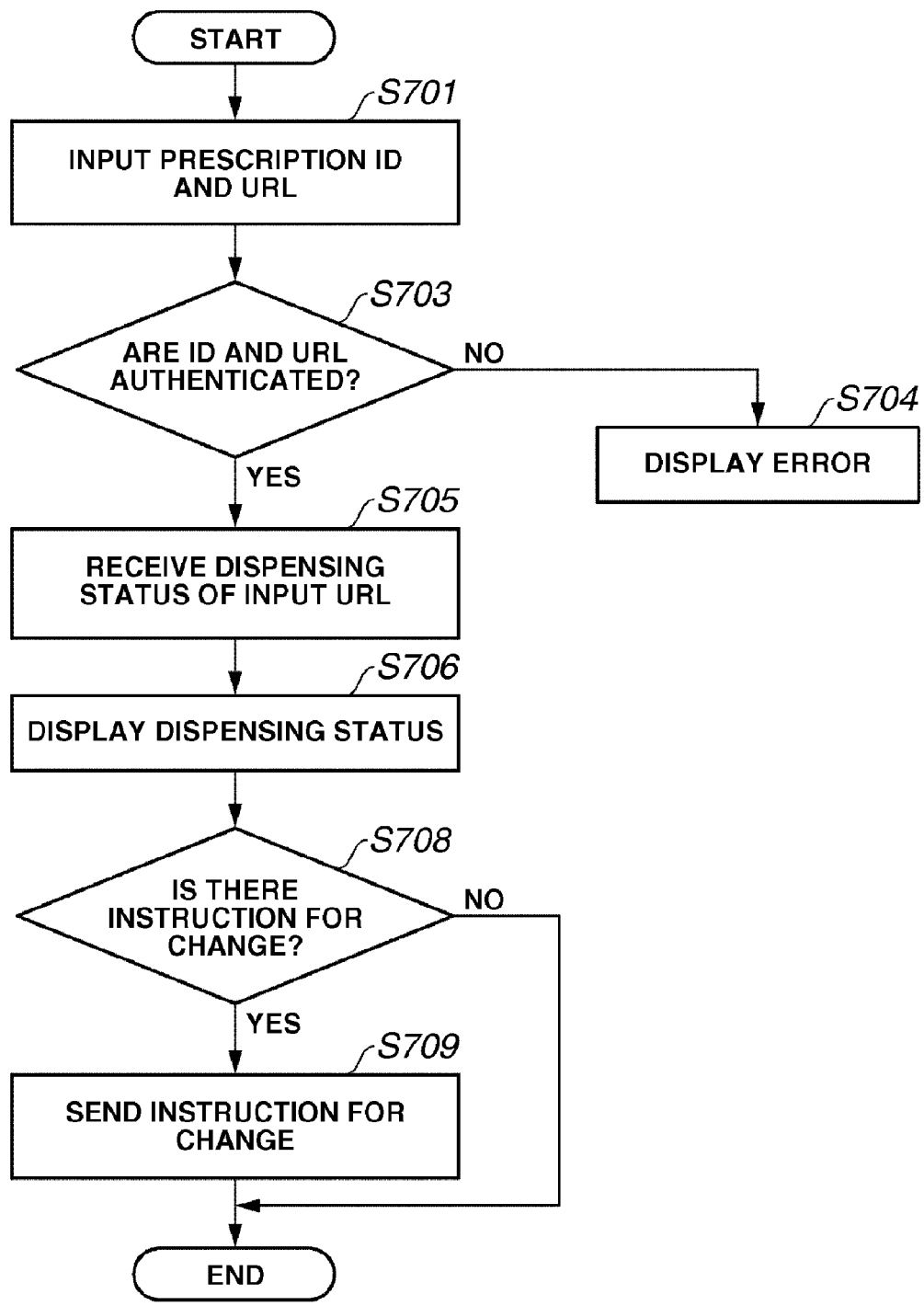
FIG. 7 is a flowchart of a process executed by an image forming apparatus or a portable terminal in the first exemplary embodiment.

FIG. 7 is a flow diagram of a process for inquiring about the dispensing status of the prescription from the image forming apparatus 104, the image forming apparatus 111, or from the patient's portable terminal 107. Hereinafter, for description purposes, the term "dispensing status confirmation terminal" will be used to refer to the above listed locations.

In step S701, the URL and the prescription ID for confirming the dispensing status of the medicine is input via the dispensing status confirmation terminal. The image forming apparatus 101 authenticates the prescription ID input in step S701 using the prescription ID stored in the prescription table 1401. In step S703, if the prescription ID and URL are authenticated, the flow proceeds to step S705. On the other hand, if prescription ID and URL are not authenticated, the flow proceeds to step S704, in which an error message is displayed. In step S705, the dispensing status confirmation terminal receives the dispensing status corresponding to the input URL.

Figure 8:
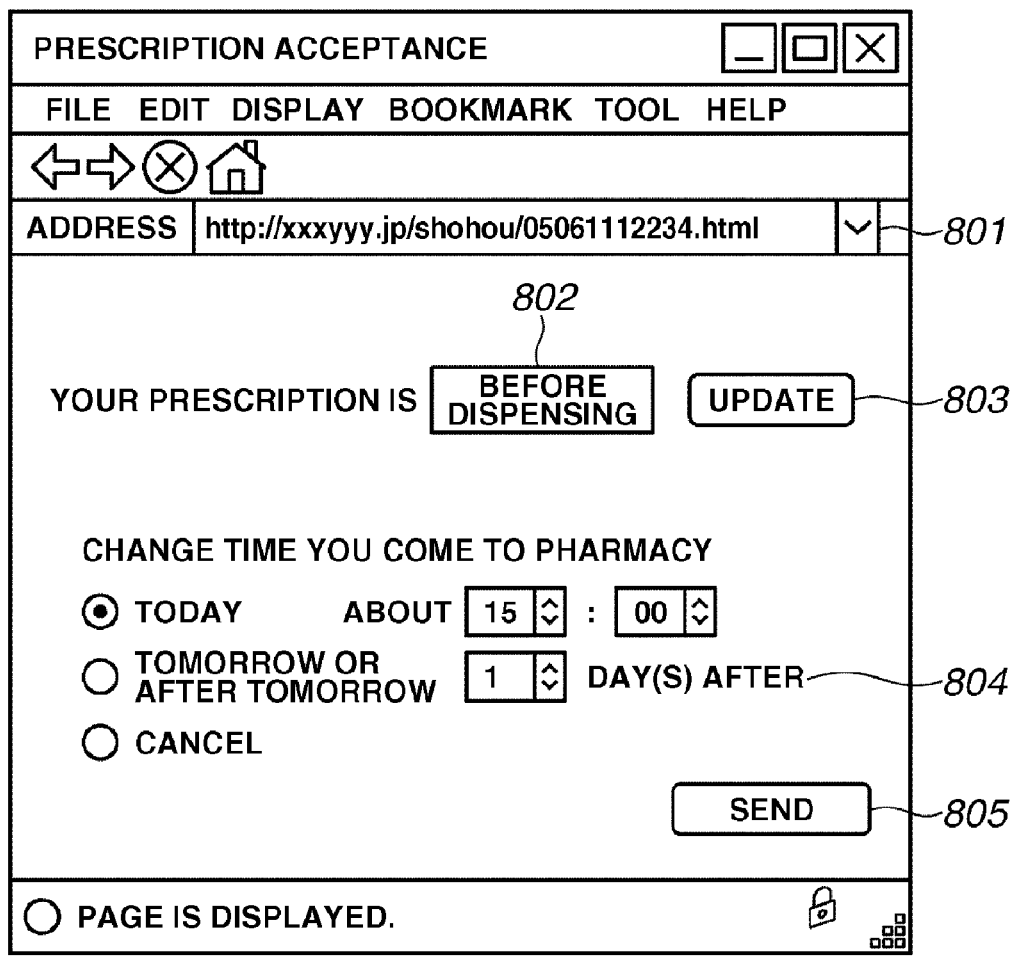
FIG. 8 illustrates an example of a user interface (UI) displayed on a display unit of the image forming apparatus or the portable terminal in the first exemplary embodiment.

Next, in step S706, the dispensing status of the prescription is displayed on the dispensing status confirmation terminal, as illustrated in FIG. 8. FIG. 8 is an example of a user interface used to display the dispensing status of a previously-sent prescription, and for a patient 401 to change the pickup time of medicine or to cancel the prescription. Reference numeral 801 denotes a specified URL address. Reference numeral 802 denotes the dispensing status of the prescription and can dynamically be changed. As previously discussed, the dispensing status 802 is "before dispensing" when the prescription has been received but not yet provided to the pharmacist, is "being dispensed" when the prescription has been given to the pharmacist, and is "already dispensed" when the prescription has been filled. A graphical control 803 can update the dispensing status. A second graphical control 804 enables the patient 401 to change the expected time the patient 401 plans on being at the pharmacy or to cancel the prescription. A third graphical control 805 sends updated information to the image forming apparatus 101.

Returning to FIG. 7, in step S708, a determination is made whether a change instruction has been inputted. If the patient 401 wants to change the expected time the patient plans on being at the pharmacy or wants to cancel the prescription, the patient selects a button for changing the time or to cancel from graphical control 804 illustrated in FIG. 8. If a new time is chosen, the patient 401 inputs the new time the patient plans on being at the pharmacy.

In step S708, if an instruction for change is input, the flow proceeds to step S709. In step S709, the dispensing status confirmation terminal sends information about the change or the cancellation to the image forming apparatus 101 and then the process ends. If in step S708, the patient 401 cancels the visit to the pharmacy, the image forming apparatus 104 deletes the prescription data corresponding to the prescription ID stored in the prescription table 1401. If, in step S708, an instruction for change is not input, the process ends.

Figure 17:
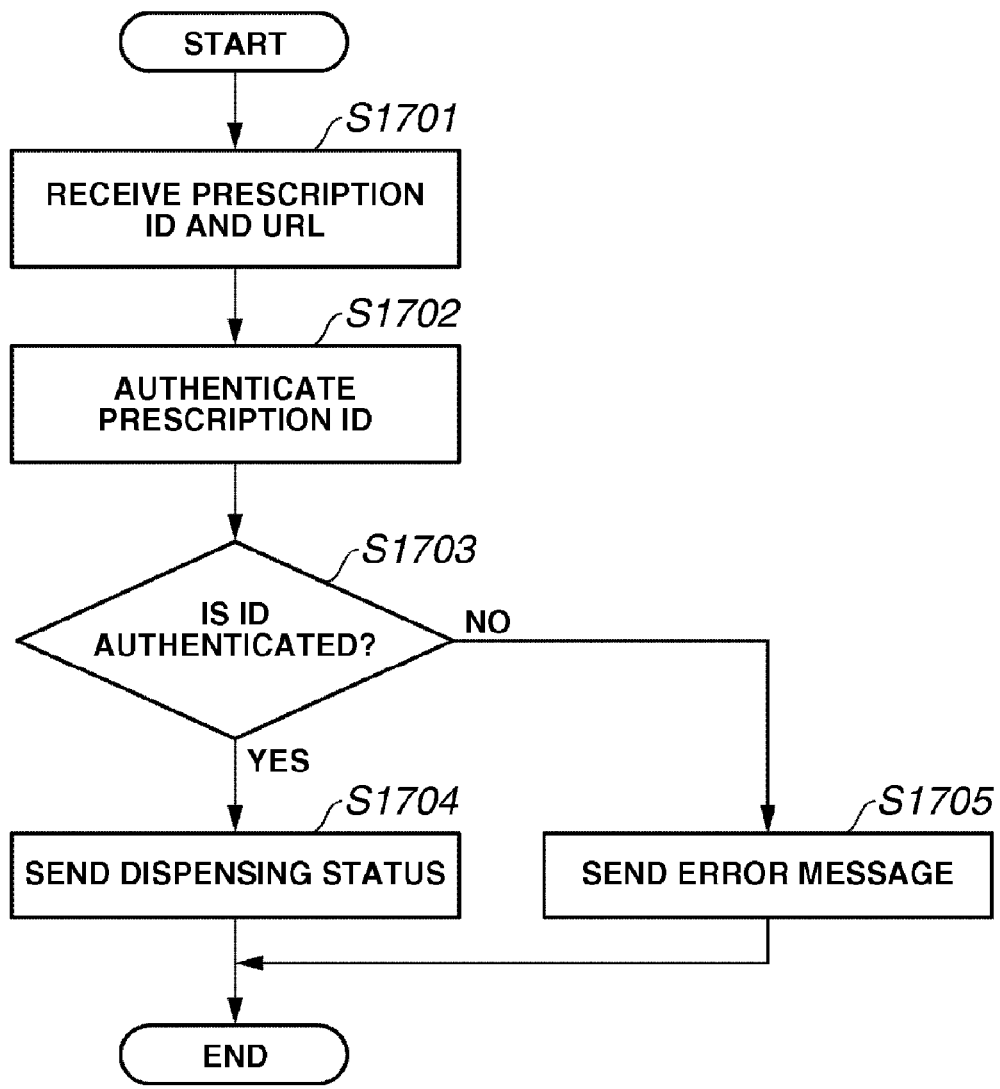
FIG. 17 is a flowchart of a process executed by an image forming apparatus in response to an inquiry about the dispensing status in the first exemplary embodiment.

FIG. 17 is a flow diagram of a process performed by the image forming apparatus 101 in response to an inquiry by the patient 401 about the dispensing status. First, in step S1701, the image forming apparatus 101 receives an inquiry about the dispensing status of the prescription from the dispensing status confirmation terminal. Specifically, in step S1701, the image forming apparatus 101 receives the prescription ID and the URL. Then, in step S1702, the image forming apparatus 101 authenticates the prescription ID received in step S1701 using the prescription ID stored in the prescription table 1401.

In step S1703, a determination is made whether the prescription ID received in step S1701 is authenticated. If the prescription ID is authenticated, the flow proceeds to step S1704. On the other hand, if the prescription ID is not authenticated, the flow proceeds to step S1705. In step S1704, the image forming apparatus 101 sends the dispensing status to the dispensing status confirmation terminal that sent the inquiry about the dispensing status. In step S1705, the image forming apparatus 101 sends an error message indicating that a wrong ID has been sent to the dispensing status confirmation terminal that sent the inquiry about the dispensing status.

In the present embodiment, a prescription is sent to an image forming apparatus in a pharmacy that is specified by a patient using an image forming apparatus in a medical institution. However, the present invention is not limited to the prescription being sent from an image forming apparatus in a medical institution. Any location that would enable a patient to send a prescription that would enable practice of the present invention is applicable.

As described above, according to the present embodiment, the dispensing status of a prescription can be determined by accessing a prescription table storing the dispensing status of the prescription after the prescription has been sent to a pharmacy specified by a patient from a medical institution. This provides dispensing time of a prescription to a patient even if prescriptions are not dispensed in a sequential order due to the prescription contents or in the case of an emergency.

Furthermore, a patient can change the pickup time for a prescription or can cancel the prescription even after the prescription has been sent to the pharmacy. Thus, in the case of changing the pickup time, the patient can pickup the medicine at a time that is convenient for the patient.

Second Exemplary Embodiment

In the above-described first exemplary embodiment, a patient submits an inquiry to obtain the dispensing status from the prescription table when the patient wants to know the dispensing status of the prescription which has already been sent to the pharmacy.

In a second exemplary embodiment of the present invention, the image forming apparatus 101 automatically informs the portable terminal 107 that the prescription has been filled or delayed in accordance with the dispensing status of the prescription.

Figure 18:
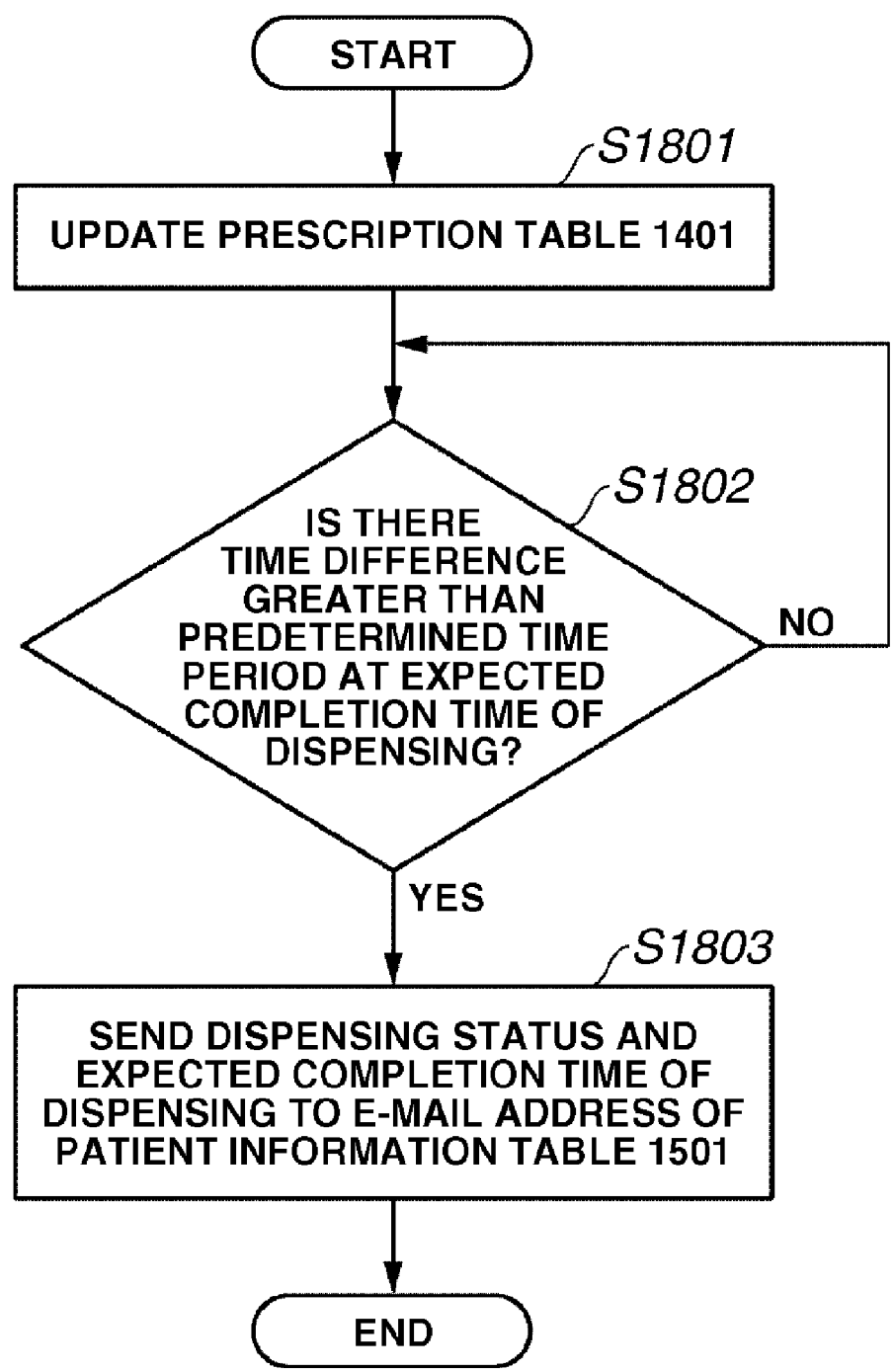
FIG. 18 is a flowchart of a process executed by an image forming apparatus in a second exemplary embodiment.

FIG. 18 illustrates a process flow performed by the image forming apparatus 101 in the present embodiment.

In step S1801, the prescription table 1401 is updated by accessing the prescription table 1401 using the image forming apparatus 101 or the data processing apparatus 108. Next, in step S1802, the image forming apparatus 101 determines whether there is a change in the expected time to complete filling the prescription stored in the prescription table 1401. If there is a change greater than a predetermined period of time, the flow proceeds to step S1803. On the other hand, if there is no change or the change is less than a predetermined time, the process remains at step S1802 until a change greater than a pre determined time is detected. In step S1803, the image forming apparatus 101 sends the dispensing status and the expected dispensation completion time to an e-mail address in the patient information table 1501.

As described above, according to the present embodiment, the image forming apparatus 101 automatically informs the portable terminal 107 of the patient about the change in the dispensing status, without the patient inquiring about the dispensing status of the prescription. The patient can be made aware of any changes in the dispensing status, e.g., change due to an interruption occurring as a result of an emergency case, thus, the patient is provided up-to-date dispensing status.

Third Exemplary Embodiment

In the above-described first exemplary embodiment, the patient can input any expected time the patient plans on being at the pharmacy as long as the time is after the expected waiting time, and the time is within the business hours of the pharmacy. According to a third exemplary embodiment, different time periods for a patient to come to the pharmacy are provided between patients whose illness (e.g., a cold) can be transmitted to others and patients whose illness (e.g., high blood pressure) cannot be transmitted to others. Establishing different time periods based on type of illness allows for a lower possibility of transmitting diseases among patients in a pharmacy.

The process associated with the present embodiment is similar to the process illustrated in FIG. 5 of the first exemplary embodiment, except for one function. Specifically, in step S509 of FIG. 5, when the patient inputs the expected time to come to the pharmacy via the operation unit 204 of the image forming apparatus 104, the patient cannot select a predetermined time period depending on the patient's illness. In the present embodiment, the image forming apparatus 104 receives the waiting time of each pharmacy in step S506 of FIG. 5, together with a time period specified by patients whose illness (e.g., a cold) can be transmitted to others and a time period specified by patients whose illness (e.g., suffering a fracture) cannot be transmitted to others.

A list of the external pharmacies is then displayed in step S507, and the patient inputs a destination external pharmacy in step S508. In step S509, a limited time period in which the patient can come to the pharmacy is provided based on the illness stored in the patient information table 1501, and the patient inputs an available time period in which the patient plans to be at the pharmacy. In another embodiment, the limited time period in which the patient can come to the pharmacy may be determined based on the contents of the medications described on the prescription or the name of the disease written on the prescription. Setting of the limited time period is not limited to the above described criteria, and any criteria for setting the limited time period that would enable practice of the present invention is applicable.

Fourth Exemplary Embodiment

In the above-described first exemplary embodiment, the same expected waiting time is provided to each patient, regardless of the disease type. In a fourth exemplary embodiment of the present invention, the expected waiting time varies based on the type of or seriousness of the disease. Thus, when the prescription is sent, a shorter waiting time is set for a patient with a more serious case than the waiting time of other patients.

The process of the present embodiment is similar to the process illustrated in FIG. 5 of the first exemplary embodiment, except for one function. Specifically, according to the present embodiment, in step S505 of FIG. 5, the display unit 209 displays a priority waiting time as illustrated in FIG. 9, where the priority waiting time is shorter than the normal waiting time. That is, in step S506, the priority waiting time set for a patient with a more serious case is received together with the normal waiting time. In step S507, the priority waiting time is displayed instead of the normal waiting time when it is determined that the patient is one with a more serious case based on the name of disease stored in the patient information table 1501. On the other hand, when it is determined that the patient is not one with a more serious case, the normal waiting time as illustrated in FIG. 10 is displayed.

Fifth Exemplary Embodiment

In the first exemplary embodiment, the image forming apparatus 101 in the pharmacy receives a prescription, and the pharmacist dispenses the prescribed medicine. In a fifth exemplary embodiment of the present invention, upon receipt of a prescription, the image forming apparatus 101 searches for a medicine currently prescribed for the patient associated with the received prescription from a medicine history server that contains information regarding the medicine currently prescribed for the patient.

The image forming apparatus 101 then determines whether there are any potential effects of the patient taking the medicine currently prescribed with the medicine being prescribed on the received prescription. If it is determined that an unwanted effect could occur as a result of taking both medicines together, the image forming apparatus 101 sends a request to change the newly prescribed medicine to a different medicine that can safely be taken with the currently prescribed medicine to the image forming apparatus 104 in the medical institution. If a new medicine is prescribed, it is then re-sent to the image forming apparatus 101.

Figure 19:
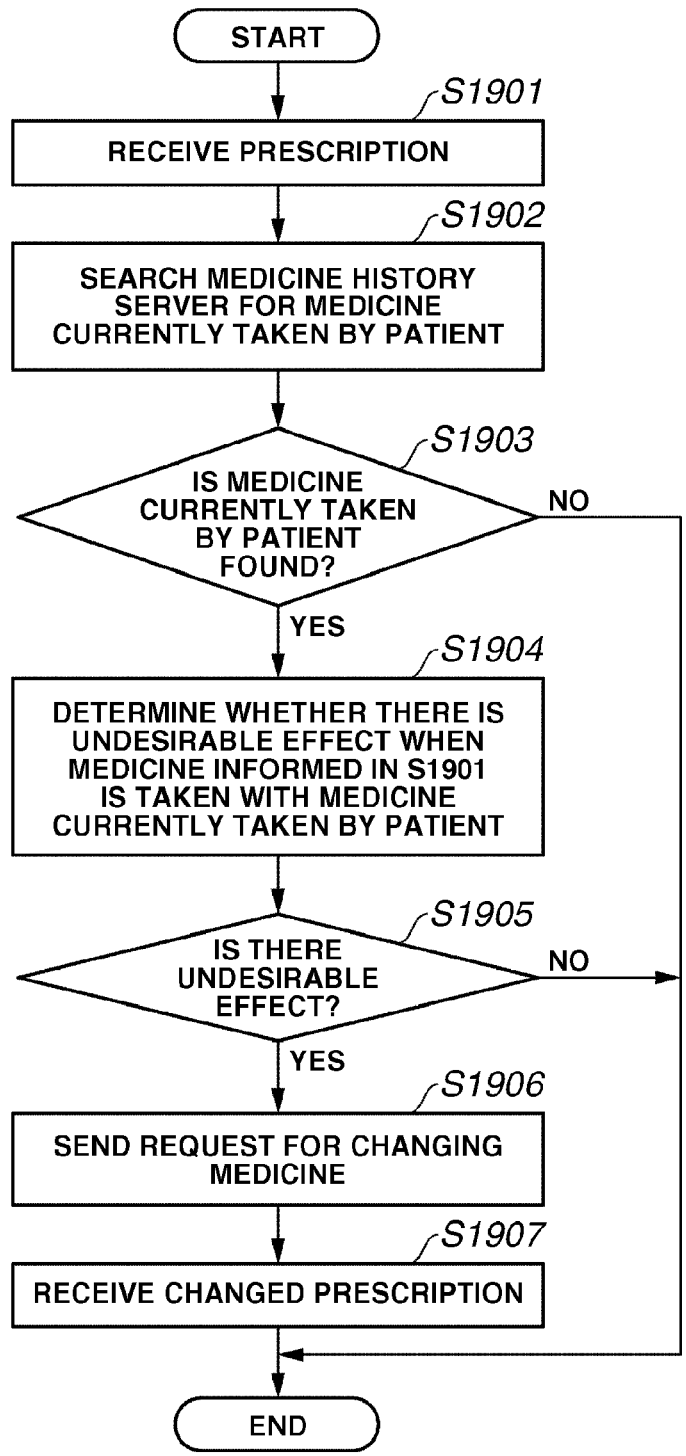
FIG. 19 is a flowchart of a process executed by an image forming apparatus in a pharmacy in a fifth exemplary embodiment.

FIG. 19 is a flow diagram of a process performed by the image forming apparatus 101 to determine whether a newly prescribed medication is compatible with a currently prescribed medication.

First, in step S1901, the image forming apparatus 101 receives a prescription sent from the image forming apparatus 104. Next, in step S1902, the image forming apparatus 101 searches the medicine history server for a medicine currently prescribed for the patient based on an insurance number of the prescription data received in step S1901. Note that the medicine history server stores information regarding medicines currently prescribed for patients and is set in the pharmacy. The medicine history server can be set outside the pharmacy so as to manage medicine information regarding patients of a plurality of pharmacies. In step S1903, if the image forming apparatus 101 finds medicine currently prescribed for the patient, the flow proceeds to step S1904. On the other hand, if the image forming apparatus 101 does not find any medicine currently prescribed for the patient, the process ends.

In step S1904, the image forming apparatus 101 determines whether there are any effects when a medicine written on the prescription received in step S1901 is taken with a medicine obtained from the medicine history server. In step S1905, if it is determined that there is an undesirable effect can occur when both medicines are taken together, the flow proceeds to step S1906. On the other hand, if it is determined that there are no undesirable effects when both medicines are taken together, the process ends.

In step S1906, the image forming apparatus 101 sends a request to change the medicine to a different one to the image forming apparatus 104. If new prescription for a different medicine is prepared by the medical institution, the image forming apparatus 101 receives the changed prescription data for the different medicine from the image forming apparatus 104.

Sixth Exemplary Embodiment

In the first exemplary embodiment, the image forming apparatus 101 in the pharmacy receives a prescription and creates a prescription ID corresponding to the prescription and a URL for confirming the dispensing status. In a sixth exemplary embodiment of the present invention, the image forming apparatus 101 creates an effect table showing effects of the medicine in association with dosage regimens in addition to the prescription ID and the URL, and prints a medicine effect table after the medicine has been dispensed.

Figure 20:
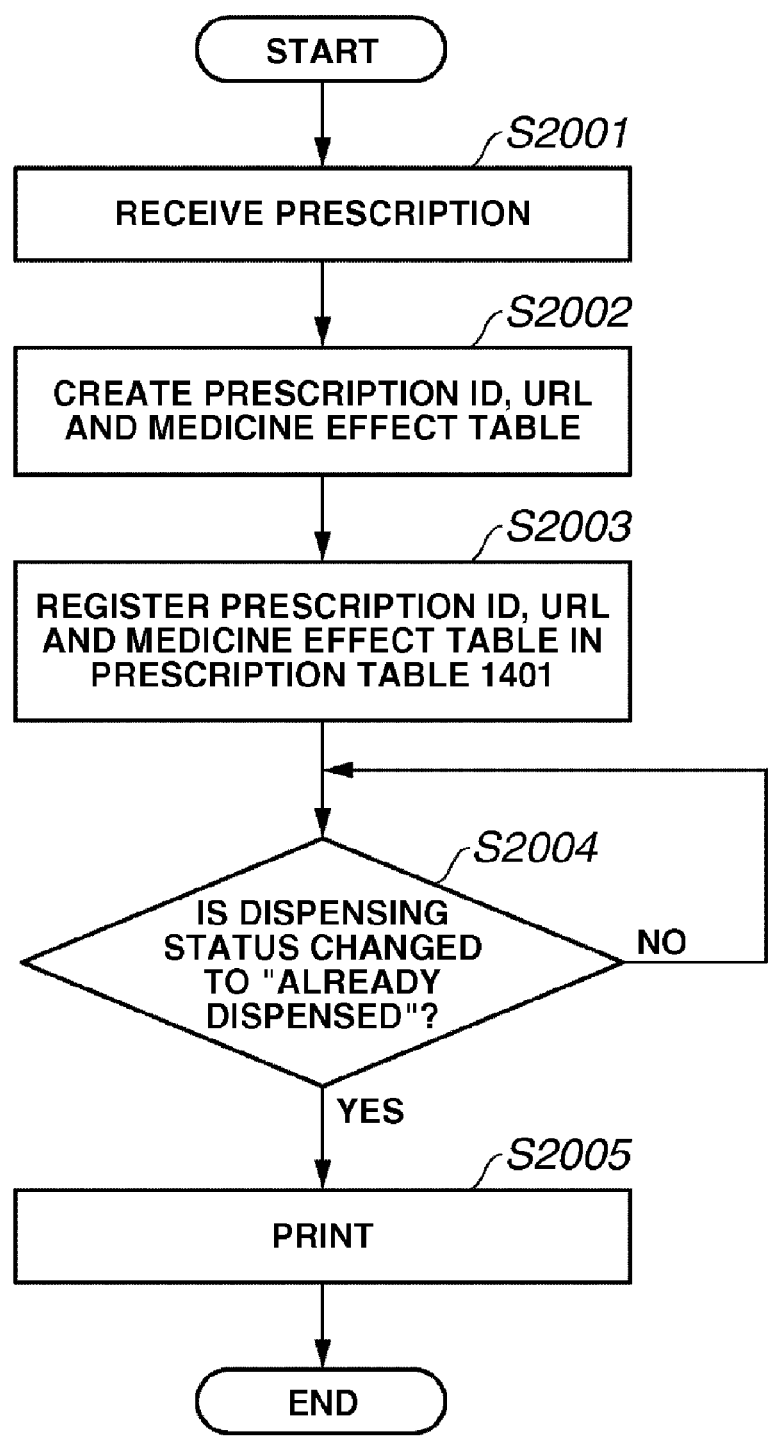
FIG. 20 is a flowchart of a process executed by an image forming apparatus in a pharmacy in a sixth exemplary embodiment.

FIG. 20 is a flow diagram of a process performed by the image forming apparatus 101 in the sixth exemplary embodiment. According to the sixth embodiment, a medicine effect table is created based on a received prescription, thus eliminating possible input errors when manually creating an effect table with reference to the original prescription.

In step S2001, the image forming apparatus 101 receives a prescription sent from the image forming apparatus 104 of the medical institution. Then, in step S2002, the image forming apparatus 101 creates a specific prescription ID for the received prescription, and creates a URL for confirming the prescription ID and the dispensing status of the prescription. In addition, the image forming apparatus 101 also creates an effect table based on the prescription received in step S2001. In step S2003, the image forming apparatus 101 registers a patient name, a prescription ID, a URL, a dispensing status, an insurance number, and an effect table (i.e., information about the medicine) in the prescription table 1401 of the storage unit 211.

In step S2004, the image forming apparatus 101 checks whether the dispensing status has been updated to "already dispensed" in the prescription table 1401. If the dispensing status has been updated to "already dispensed", the flow proceeds to step S2005, where printing of the effect table stored in the prescription table 1401 occurs. FIG. 21 is an example illustrating the effect table printed in step S2005. In step S2004, if the status has not been updated to "already dispensed", the process remains at step S2004 until the status is updated.

Additional Exemplary Embodiments

In another embodiment, instead of a patient submitting the prescription to a pharmacy, the prescription is initially submitted by a member of a medical institution, such as the patient's physician.

In still another embodiment, when the patient wishes to change which pharmacy the prescription is to be picked up at, the change in pharmacies is authorized either by a member of the medical institution (e.g., the patient's physician) where the prescription was prescribed or by a staff member at the pharmacy where the prescription was originally submitted.

In still yet another embodiment, a FAX device or any other type of data transmission/reception apparatus can be used to send and receive prescription data through a network in place of the image forming apparatuses used in the above-described exemplary embodiments. After the prescription is read, the prescription data can be sent to a data processing apparatus such as a PC installed in the medical institution and may be sent to the pharmacy from the data processing apparatus via electronic mail.

The present invention can also be accomplished by a computer (or a CPU) of a system or device reading and executing program code stored on a storage medium storing the program code of software for realizing the functions of the above-described exemplary embodiments. In this case, the program code read from the storage medium realizes the functions of the above-described exemplary embodiments. Thus, the program code or the storage medium storing the program code is included in the present invention. The storage medium for providing the program code may, for example, be a floppy disk, a hard disk, an optical disk, a magneto-optical disk, a CD-ROM, a CD-R, a DVD-ROM, a DVD-R, a magnetic tape, a non-volatile memory card, a ROM. Further, the storage medium for providing the program code may be any of a storage medium included in a file server on a network, a storage medium included in an FTP server on the Internet, and the like.

Executing the program code read by the computer results in realization of the functions of the above-described exemplary embodiments. In addition to the functions, an operating system (OS) operating on the computer partially or entirely executes the actual processing based on an instruction of the program code, thus realizing the functions of the above-described exemplary embodiments. Such a case is also included in the present invention.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2005-352208 filed Dec. 6, 2005, which is hereby incorporated by reference herein in its entirety.

What is claimed is:

1. An image forming apparatus including a scanner unit and a printer unit, comprising:
   a patient information input unit configured to input patient information of a patient;
   a controller unit configured to authenticate patient information using previously stored patient information;
   a receiving unit configured to receive, from at least one other device when the patient information is authenticated, both a patient dispensing waiting time and a patient priority waiting time, wherein the patient dispensing waiting time is a time that the at least one other device estimates a patient will need to wait before receiving a filled prescription as measure from a time in which the patient information is authenticated to that time in which a filled prescription is delivered to the patient without also being administered to the patient, and wherein the patient priority waiting time is a time based on the patient dispensing waiting time that further takes into account a name of a disease such that the patient priority waiting time is shorter than the patient dispensing waiting time; and
   a display unit configured to, when it is determined that the patient is a patient with a more serious case based on a name of a disease included with the patient information, display the patient priority waiting time received by the receiving unit instead of displaying the patient dispensing waiting time.

2. An information processing apparatus according to claim 1, wherein the display unit further is configured to display a name of a pharmacy corresponding to the patient priority waiting time and business hours of the pharmacy.

3. An information processing apparatus according to claim 1, further comprising:
   a time input unit configured to input, after the patient priority waiting time is displayed by the display unit, a patient expected arrival time that represents a time the patient expects to be at a pharmacy to pick up a filled prescription, wherein the patient information is stored in a patient information table.

4. An information processing apparatus according to claim 1, wherein the patient information describes a medicine prescribed for the patient as a result of a diagnosis in a medical institution, and wherein a pharmacy that receives the patient information is external to the medical institution.

5. An information processing apparatus according to claim 1, wherein the patient information is included in a prescription received by a pharmacy and the patient dispensing waiting time is updated over time as a function of a number of prescriptions received over time by the at least one other device, whereby the patient dynamically can be made aware of a general dispensing (preparation) status of the prescription in the pharmacy in real time.

6. An information processing apparatus according to claim 1, wherein the patient information is included in a prescription and wherein the time in which a filled prescription is delivered to the patient substantially equals that time at which the prescription becomes a filled prescription.

7. An information processing apparatus according to claim 1, wherein the patient information is included in a prescription and wherein the patient dispensing waiting time is updated over time as a function of at least one of (i) whether the prescription has been given to a pharmacist for filling, (ii) whether a pharmacist that received the prescription has filled the prescription, and (iii) whether the patient corresponding to the patient information is located in a position to receive the filled prescription.

8. An information processing apparatus according to claim 1, wherein the patient information is included in a prescription received by a pharmacy and wherein the patient dispensing waiting time is updated over time as a function of a patient expected arrival time received from the patient that represents a time the patient expects to be at the pharmacy.

9. An information processing apparatus according to claim 8, wherein the patient expected arrival time is restricted based on the name of the disease included with the patient information.

10. An information processing apparatus according to claim 8, wherein the patient expected arrival time input by patient is restricted based on contents of medications described in the prescription.

11. An information processing apparatus according to claim 9, wherein the patient expected arrival time is restricted based on whether the name of the disease included with the patient information is of a disease that can be transmitted to other people.

12. An information processing apparatus according to claim 1, wherein if the name of the disease included with the patient information is of a disease that can be transmitted to other people, then it is determined that the patient is a patient with a more serious case.

13. An image forming apparatus including a scanner unit and a printer unit, comprising:
    a patient information input unit configured to input patient information of a patient;
    a controller unit configured to authenticate the patient information using previously stored patient information;
    a receiving unit configured to receive, from at least one other device when the patient information is authenticated, both a patient dispensing waiting time and a time period configured to be specified by a patient having an illness;
    a display unit configured to display the patient dispensing waiting time received by the receiving unit; and
    a time input unit configured to input, after the patient dispensing waiting time is displayed by the display unit, a patient expected arrival time that represents a time the patient expects to be at a pharmacy to pick up a prescription that is filled based on the patient information,
    wherein the patient expected arrival time is limited in accordance with a disease type included in the patient information input by the patient information input unit and a time period configured to be specified by a patient having an illness received by the receiving unit.

14. A method for using an image forming apparatus including a scanner unit and a printer unit to manage dispensing status information associated with a prescription for a medicine, the method comprising:
    inputting patient information of a patient via an operation unit;
    authenticating patient information using previously stored patient information;
    receiving, from at least one other device when the patient information is authenticated, both a patient dispensing waiting time and a patient priority waiting time, wherein the patient dispensing waiting time is a time that the at least one other device estimates a patient will need to wait before receiving a filled prescription as measure from a time in which the patient information is authenticated to that time in which a filled prescription is delivered to the patient without also being administered to the patient, and wherein the patient priority waiting time is a time based on the patient dispensing waiting time that further takes into account a name of a disease such that the patient priority waiting time is shorter than the patient dispensing waiting time; and displaying, when it is determined that the patient is a patient with a more serious case based on a name of a disease included with the patient information, the received patient priority waiting time instead of displaying the patient dispensing waiting time.

15. The method according to claim 14, wherein displaying includes displaying a name of a pharmacy corresponding to the patient priority waiting time and business hours of the pharmacy.

16. The method according to claim 14, further comprising:

inputting, after the patient priority waiting time is displayed, a patient expected arrival time that represents a time the patient expects to be at a pharmacy to pick up a filled prescription, wherein the patient information is stored in a patient information table.

17. A method for using an image forming apparatus including a scanner unit and a printer unit to manage dispensing status information associated with a prescription for a medicine, the method comprising:

inputting patient information of a patient via an operation unit;

authenticating the patient information using previously stored patient information;

receiving, from at least one other device when the patient information is authenticated, both a patient dispensing waiting time and a time period configured to be specified by a patient having an illness;

displaying the patient dispensing waiting time received; and inputting, after the patient dispensing waiting time is displayed, a patient expected arrival time that represents a time the patient expects to be at a pharmacy to pick up a prescription that is filled based on the patient information, wherein the patient expected arrival time is limited in accordance with a disease type included in the input patient information and a received time period configured to be specified by a patient having an illness.

* * * * *